United States Patent [19]

Nakagawa et al.

[11] 4,423,034
[45] Dec. 27, 1983

[54] PROCESS FOR THE PREPARATION OF ANTIBODIES

[75] Inventors: Nobuaki Nakagawa; Kikuo Kotani; Shigeo Katsuragi; Kaoru Morita; Kunio Ohyama; Toshiharu Noda, all of Shizuoka, Japan

[73] Assignee: Toyo Jozo Kabushiki Kaisha, Shizuoka, Japan

[21] Appl. No.: 372,824

[22] Filed: Apr. 28, 1982

Related U.S. Application Data

[62] Division of Ser. No. 197,535, Oct. 16, 1980, abandoned.

[51] Int. Cl.³ .................. A61K 39/00; C07G 7/00; C07C 103/52
[52] U.S. Cl. .................. 424/85; 260/112 R; 260/112.5 R; 436/547
[58] Field of Search .................. 260/112.5 R, 112 R; 424/85

[56] References Cited

U.S. PATENT DOCUMENTS 3,642,763  2/1972  Wunsch et al. ............ 260/112.5 R
4,201,770  5/1980  Stevens .................... 260/112.5 R
4,206,199  6/1980  Fujino et al. .............. 260/112.5 R

OTHER PUBLICATIONS

Chem. Abstr., vol. 93, 1980, p. 72244a.
Chem. Abstr., vol. 93, 1980, p. 161615q.
Chem. Abstr., vol. 92, 1980, p. 88302h.
Chem. Abstr., vol. 89, 1978, p. 180345k.
Chem. Abstr., vol. 90, 1979, p. 184634x.
Chem. Abstr., vol. 80, 1974, p. 10762r.
Chem. Abstr., vol. 79, 1973, p. 62885g.

*Primary Examiner*—Delbert R. Phillips
*Attorney, Agent, or Firm*—Young & Thompson

[57] ABSTRACT

A novel peptide of the formula

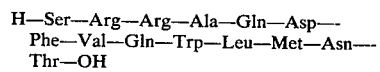

is the 16–29 fragment of glucagon and can be conjugated with a protein such as albumin or modified albumin using glutaraldehyde or 3-(2'-benzothiazolyldithio) propionate succinimide ester as a conjugation reagent. The conjugated peptide can be used to sensitize a mammal by administering the conjugated peptide subcutaneously, after which the blood is collected from the mammal and antibodies concentrated from the blood, which antibodies are then useful in assay methods for trace amounts of glucagon in human blood.

2 Claims, No Drawings

PROCESS FOR THE PREPARATION OF ANTIBODIES

This application is a division of application Ser. No. 197,535, filed Oct. 16, 1980, now abandoned.

This invention relates to the preparation of specific antibodies by sensitizing a mammal by administering to the mammal a glucagon fragment of the formula

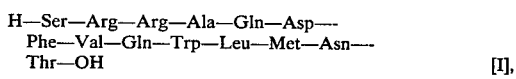

in a conjugated form of the said glucagon fragment and protein.

Glucagon is a hormone which acts on carbohydrate metabolism, and has been analyzed as a 1-29 peptide of the pancreas of the formula

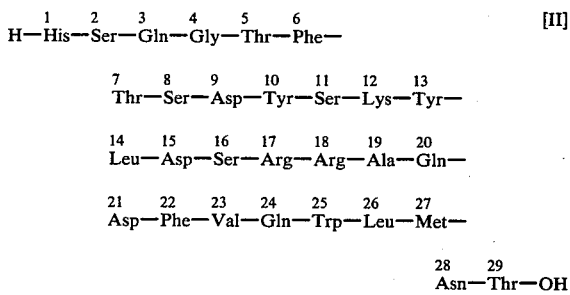

[hereinafter designated as glucagon(1-29)] and the determination of its level in human blood has been very important for clinical assay.

Radioimmunoassay, fluorescent immunoassay, enzyme immunoassay and the like assay methods based on immune reactions have been used as the major assay methods for trace amounts of glucagon in human blood, and therefore its specific antibody has been essentially required.

However, the specific antibody for glucagon can only be obtained incidentally by using a combination of glucagon(1-29) as hapten and bovine serum albumin (BSA). Moreover, its reproducibility of results is unreliable.

Furthermore, few examples of the production of the antibody using a combination of hapten such as a fragment of glucagon(1-29), for example a glucagon fragment consisting of peptide(18-29) in glucagon, or a glucagon fragment consisting of peptide (19-29) in glucagon [hereinafter designated as glucagon(19-29), Japanese patent non-examined Publication No. 53-99320] or a glucagon fragment consisting of peptide(15-29) in glucagon (Japanese patent non-examined Publication No. 54-24868), and BSA have been reported.

We have devised a method for obtaining effective antibodies in an assay based on the immune reaction of glucagon(1-29), and found that the combination of protein and a novel glucagon fragment consisting of peptide(16-29) in glucagon, produced its antibody effectively, and that the said antibody reacts advantageously with labelled glucagon(1-29) and various labelled glucagon fragments in immune reactions.

Still another object of the present invention is to provide a process for producing specific antibodies using the combination of glucagon(16-29) and protein.

The synthesis of glucagon(16-29) of the present invention can be carried out as follows:

an amino acid and/or lower peptide is reacted by condensation in the order of the amino acid sequence of formula [I], and the protective group for the reactive group is released at the final stage of the reaction. The condensation reaction can be carried out by conventional peptide synthesis by repeating the attaching and removal of the protective groups and condensation. The protective groups for the synthesis of the starting materials or intermediates are conventional protective groups for peptide synthesis and are easily removable by hydrolysis, acid decomposition, reduction, aminolysis or hydrazinolysis.

For example, the α-amino group may be protected conventionally by a benzyloxycarbonyl group such as benzyloxycarbonyl, p-nitrobenzyloxycarbonyl or p-methoxybenzyloxycarbonyl, or an aliphatic oxycarbonyl group such as t-amyloxycarbonyl or t-butoxycarbonyl.

The carboxyl group can be protected by esterification. The ester group is substituted with an alkanol such as methanol or ethanol, or an aralkanol such as benzylalcohol, p-nitrobenzylalcohol, p-methoxybenzylalcohol or dichlorobenzylalcohol.

The hydroxy group in serine and threonine may optionally be protected by esterification or etherification. A group protected by esterification is benzyloxycarbonyl. A group protected by etherification is benzyl.

The amino group in the guanidino group in arginine is protected by tosyl or benzyloxycarbonyl. However it is not always necessary to protect the guanidino group.

After the last of the condensations, these protective groups are split preferably by acid decomposition such as by hydrogen fluoride in a one-step removal. Therefore, the side chain reactive group in serine, arginine, aspartic acid or threonine is protected by a protective group easily removed by hydrogen fluoride.

For example, the hydroxyl group in serine and threonine is protected by benzyl; the amino group in the guanidino group in arginine is protected by tosyl; and the side chain carboxyl group in aspartic acid is protected by a benzyl ester.

Other α-amino groups and carboxyl groups are protected by a protective group which can be removed under conditions which do not remove the side chain protective group. For example, an α-amino group is preferably protected by t-butoxycarbonyl or t-amyloxycarbonyl, which can be removed by trifluoroacetic acid, or protected by benzyloxycarbonyl which can be removed by catalytic reduction. A carboxyl group is protected by a methyl or ethyl ester which can be removed with dilute aqueous sodium hydroxide, and a carboxyl group at a C-terminal is protected by a benzyl ester which can be removed with anhydrous hydrogen fluoride.

The condensation of amino acids and/or peptides is carried out for example as follows:

An amino acid or peptide having a protected α-amino group and an activated terminal carboxyl group is reacted with an amino acid or peptide having a free α-amino group and a protected terminal carboxyl group. Alternatively, an amino acid or peptide having an activated α-amino group and a protected terminal carboxyl group is reacted with an amino acid or peptide having a free terminal carboxyl group and a protected α-amino group.

The carboxyl group can be activated by, for example, conversion to an acid azide, acid anhydride, acid imidazolide, isoxazolide or active ester, or by reacting with carbodiimide or N,N'-carbonyl-diimidazole.

The preferred condensation reactions are the carbodiimide, azide or active ester method. In the condensation reaction, racemization should carefully be avoided, and the preferred methods are the azide, active ester method using succinimide ester or p-nitrophenyl ester, Wünsch method [Z. Naturforsch., 216, 426 (1966)] or Geiger method [Chem. Ber., 103, 788 (1970)], especially a modified Geiger method using N-ethyl, N'-3-dimethylaminopropyl-carbodiimide as a condensation agent.

Thus the protected peptide [I] is obtained. These protective groups are split preferably by acid decomposition such as one-step removal by hydrogen fluoride, and finally the product [I] can be obtained.

The purification of peptide [I] can be achieved by known column chromatography using a carrier.

Glucagon(16–29) of the present invention is bound with protein to produce a conjugated form for the production of antibodies. Examples of the protein conventionally used are BSA or its modification by splitting the inner molecular disulfide group with alkaline or sodium laurylsulfate and mercaptoethanol treatment.

Examples of conjugation reagents for glucagon and protein are polyfunctional conjugation reagents such as glutaraldehyde or 3-(2'-benzothiazolyl-dithio) propionate succinimide ester (refer to Japanese Patent Appln. No. 53-85900). These polyfunctional conjugation reagents are selected for functional groups which participate in the bonding of protein.

The ratio of glucagon(16–29) and protein such as BSA is one or more moles of glucagon(16–29) per mole of BSA, preferably ten moles of glucagon(16–29) per mole of BSA. In the binding reaction, the required amount of glucagon(16–29) is added to an aqueous medium of pH 7–8, and the polyfunctional conjugation reagent is added thereto. Reaction proceeds with cooling or at ambient temperature for 1–4 hours. After purifying by gel filtration, BSA is added and the mixture is reacted at ambient temperatures for 1–4 hours. A conjugated product of glucagon(16–29) and BSA is obtained after purification such as by gel filtration and dialysis, and if necessary stored after lyophilization.

The thus-obtained conjugated form of glucagon(16–29) and protein is administered in mammals such as rabbit, rat, guinea pig or mouse to sensitize them. For example, the conjugated substance is suspended in Freund's complete adjuvant and is subcutaneously injected in guinea pig at a ratio of 30–70 γ of glucagon(16–29) 4–7 times at two-week intervals. Antiserum is obtained from the blood of the sensitized animals by a conventional procedure such as blood collecting and centrifugation. The said antiserum contains a higher concentration of the specific antibody and can be stored by freezing, and can be used by aliquot dilution. The said specific antibody is immunologically bound not only labelled glucagon(1–29) but also various labelled glucagon fragments such as glucagon fragment (16–29), glucagon fragment (17–29) and glucagon fragment (19–29).

As hereinabove explained, the glucagon fragment (16–29) of the present invention is useful for antibody production in the form of a conjugation of glucagon(16–29) and a protein. The thus-obtained antibody has excellent specific binding in immune reactions and the said immune reactions are advantageously used for radio immunoassay, fluorescent immunoassay and enzyme immunoassay of glucagon(1–29) in vivo.

It has been reported (Japanese patent non-examined Publication No. 55-39702) that the glucagon fragment (15–29) has an activity to conjugate protein. However, no example of the glucagon(16–29) is mentioned in the said patent specification. Moreover, the glucagon(16–29) of the present invention is more reactive and specific as compared with the fragment(15–29) due to the N-terminal amino acid serine of glucagon(16–29).

The abbreviations in the specification mean the following:

| Ser | L-serine | Val | L-valine |
|---|---|---|---|
| Arg | L-arginine | Trp | L-tryptophane |
| Ala | L-alanine | Leu | L-leucine |
| Gln | L-glutamine | Met | L-methionine |
| Asp | L-aspartic acid | Asn | L-asparagine |
| Phe | L-phenylalanine | Thr | L-threonine |
| BOC | t-butoxycarbonyl | OBzl | benzyl ester |
| AOC | t-amyloxycarbonyl | OSU | N—hydroxysuccinimide ester |
| Z | benzyloxycarbonyl | ONP | p-nitrophenyl ester |
| Bzl | benzyl | TFA | trifluoroacetic acid |
| Tos | tosyl | NMM | N—methylmorpholine |
| OMe | methyl ester | Et$_2$O | diethyl ether |
| THF | tetrahydrofuran | DMF | dimethylformamide |
| HOBT | L-hydroxybenzotriazole | | |
| WSC | N—ethyl, N'—3-dimethylaminopropylcarbodiimide | | |

The following examples illustrate the present invention. In the examples, the following carrier and developing solvent for thin layer chromatography [TLC] are used.

[TLC]

Carrier: Merck cellulose Art 5716.
Developer:
1. butanol-pyridine-acetic acid-water (15:10:3:11)
2. upper layer of butanol-pyridine-acetic acid-water (10:3:0.1:11)
3. upper layer of butanol-pyridine-acetic acid-water (5:3:0.1:11).

Carrier: Merck silica-gel Art 5721.
Developer:
chloroform-methanol-acetic acid (95:5:3)
5. chloroform-methanol-acetic acid (80:25:2)
6. chloroform-ethanol-ethyl acetate (5:2:5)
7. chloroform-methanol-acetic acid (85:15:5).

EXAMPLE 1

Production of

H—Ser—Arg—Arg—Ala—Gln—Asp—
Phe—Val—Gln—Trp—Leu—Met—Asn—
Thr—OH

[glucagon(16–29)]:

Anisole (6 ml), ethanedithiol (0.94 ml, 10 mM) and skatole (131 mg, 1 mM) was added to 2.5 g (1 mM) of BOC—Ser(Bzl)—Arg(Tos)—Arg(Tos)—Ala—Gln—Asp(OBzl)—Phe—Val—Gln—Trp—Leu—Met—Asn—Thr(Bzl)—OBzl.

The mixture was added to anhydrous hydrogen fluoride (HF, 20 ml), stirred at 0° C. for one hour, and HF was rapidly distilled off in vacuo. Et$_2$O (100 ml) was added to the residue to separate the precipitate. The precipitate was dissolved in 50–80% acetic acid (100 ml) and centrifuged. The supernatant was freeze dried to obtain the powder (1.22 g). The powder was dissolved in 8 M aqueous urea (150 ml) and adjusted to pH 9 by adding aqueous ammonia. The solution was charged on a column of carboxymethyl cellulose (4×20 cm) equilibrated with 8 M aqueous urea. After 30 minutes, the column was washed completely with water to remove urea, and eluted with continuous concentration gradient procedure using water (1 lit.) adjusted to pH 4.5 by acetic acid to aqueous 0.2 M ammonium acetate (pH 4.5, 1 lit.) Thereafter the column was eluted with aqueous 0.5 M ammonium acetate (pH 4.5, 500 ml), and finally eluted with aqueous 0.5 M ammonium acetate (pH 4.5) containing 8 M urea to fractionate the active fractions II (Nos. 80–110 tubes), III (Nos. 120–170 tubes), IV (Nos. 171–230 tubes) and V (Nos. 231–290 tubes) in fractions of 7 ml each, and these active fractions were freeze dried.

The dried powder prepared from the active fraction V was dissolved in 50% acetic acid (50 ml). Thioglycolic acid (2.5 ml) was added to the solution which was allowed to stand at 45° C. for 21 hours. Urea (24 g) was dissolved in the said solution. The insoluble part was removed by filtration. The filtrate was charged on a column (4.2×104 cm) of Sephadex LH-20 (trade name) and eluted with 50% acetic acid. Fractions Nos. 62–79 tubes, each fraction being 7 ml, were collected and freeze dried to obtain the powder (150 mg). TLC: $Rf_1=0.50$, $Rf_2=0.34$.

The lyophilized powder obtained from the active fraction IV was dissolved in 50% acetic acid (20 ml), and thioglycolic acid (1 ml) was added thereto and the mixture was allowed to stand at 45° C. for 21 hours. Urea (9.6 g) was dissolved in this solution and insoluble material was removed by filtration. The filtrate was charged on a column (3.3×120 cm) of Sephadex LH-20 (trade name) and eluted with 50% acetic acid. Active fractions of Nos. 32–37 tubes, each fraction being 7 ml, were collected and freeze dried to obtain the powder (110 mg).

TLC: $Rf_1=0.50$.

Amino acid analysis: Asp 2.03 (2), Thr 0.96 (1), Ser 0.87 (1), Glu 2.07 (2), Ala 1.02 (1), Val 0.91 (1), Met 0.95 (1), Leu 1, Phe 0.95 (1), Arg 2.19 (2), Trp 1.04 (1).

The lyophilizates obtained from the active fractions III and II were treated and subjected to column chromatography by the same procedure as the active fractions IV hereinabove to obtain a powder (130 mg) (TLC: $Rf_1=0.50$) from the fractions Nos. 31–36 tubes of the active fraction III and a powder (50 mg) (TLC: $Rf_1=0.50$) from the fractions Nos. 39–44 tubes of the active fraction II.

EXAMPLE 2

Conjugated form of glucagon(16–29) and BSA or modified BSA:

(1) Conjugated form of glucagon(16–29) and BSA:

Glucagon(16–29) (15 mg) was dissolved in 0.0001 N sodium hydroxide and adjusted to pH 8.0 to prepare a solution (20 ml). Aqueous 25% glutaraldehyde (1.5 ml) was added to the solution and reacted at room temperature for two hours. The reaction mixture was passed through a column (5×50 cm) of Sephadex G-15 and the passed fraction was collected as a solution containing about 11 mg of derivative wherein glutaraldehyde was reacted with the terminal amino group of glucagon(16–29).

BSA (42 mg, product of Sigma Co.) was added thereto and the mixture was reacted at room temperature for two hours. The reaction mixture was dialyzed in distilled water and the dialyzate was lyophilized to obtain a conjugated form of glucagon(16–29) and BSA [bound molar ratio of BSA: glucagon(16–29)=about 1:10]. Yield: 48 mg.

(2) Conjugated form of glucagon(16–29) and modified BSA:

Glucagon(16–29) (15 mg) was dissolved in 0.0001 N sodium hydroxide and adjusted to pH 8.0 to prepare a solution (20 ml). 0.1% dimethylformamide solution of 3-(2'-benzothiazolyl-dithio) propionate succinimide ester (1.575 ml) was added to the solution and the mixture was reacted at 5° C. for one hour. The reaction mixture was passed through a column (5×50 cm) of Sephadex G-15 packed with acetate buffer (pH 5) containing dimethylformamide to collect the passed fraction, a solution containing a derivative (11.5 mg) wherein a 3-(2'-benzothiazolyl-dithio) propionyl group was introduced in the terminal amino group of glucagon(16–29). The solution was adjusted to pH 7.0 and modified BSA (45 mg), previously treated with sodium lauryl sulfate and mercaptoethanol at room temperature overnight, was added thereto and the mixture was reacted at room temperature for one hour. The reaction mixture was dialyzed in distilled water and lyophilized to obtain a conjugated form of glucagon(16–29) and modified BSA [bound ratio: modified BSA: glucagon(16–29)=about 1:10]. Yield: 52 mg.

The above glucagon(16–29) was replaced by glucagon(17–29), glucagon(19–29) and glucagon(1=29) (product of Sigma Co.), and treated as the same way to obtain conjugated forms of BSA or modified BSA and glucagon(17–29), glucagon(19–29) or glucagon(1–29).

EXAMPLE 3

I. Antibody production using the conjugated form of glucagon(16–29) and BSA:

(1) The conjugated form of glucagon(16–29) and BSA (1 mg) [248 γ as glucagon(16–29)] was dissolved in 1.0 ml of 10 mM phosphate buffer (pH 7.2) (containing 0.15 M NaCl). Freund's complete adjuvant (1.0 ml) was added thereto and mixed thoroughly to obtain an emulsion.

The emulsion (0.5 ml; was injected in a skin of a finger of a foot and several subcutaneous parts of the back of a guinea pig. The same amount of emulsion was subcutaneously injected six times at two-week intervals. After 10 days from the final injection, whole blood was collected from the guinea pig and allowed to stand for 60 minutes to coagulate. Anti-glucagon(16–29) serum was obtained by centrifugation at 3000 r.p.m. for 10 minutes.

(2) The conjugated form of glucagon(17–29) and BSA (1 mg), conjugated form of glucagon(19–29) and BSA (1 mg), and conjugated form of glucagon(1–29) and BSA (2.5 mg) obtained in Example 2 were used and treated by the same procedures in Example 3(1). Anti-glucagon(17–29) serum, anti-glucagon(19–29) serum and anti-glucagon(1–29) serum were obtained.

II. Immune reactivity of antiserum:

(1) Assay method of immune reactivity:

The above antisera were diluted 200, 400, 800, 3200, 6400, 12800, 25600 and 51200 times with 10 mM phosphate buffer (pH 7.4)(containing 0.25% BSA, 1 mM $MgCl_2$, 0.1% $NaNO_3$, 3 mM EDTA and 0.15 M NaCl). Each 100 μl thereof were reacted with 100 μl of phosphate buffer solution (the same composition as the above) of labelled glucagon(1–29) or labelled glucagon fragment [label: β-galactosidase, glucagon fragment: glucagon(16-29), glucagon(17-29), glucagon(19-29)] at 5° C. for 16 hours. Guinea pig IgG (4 γ) and anti-guinea pig IgG rabbit serum were added thereto and incubated for one hour at room temperature. The precipitate was collected by centrifugation at 3000 r.p.m. for 10 minutes, and was added to 200 μl of 10 mM phosphate buffer (pH 6.7) (containing 0.1% BSA, 1 mM MgCl₂, 0.1% NaNO₃ and 0.16 M NaCl) containing 5 mg/ml of o-nitrophenyl-β-D-galactopyranoside and incubated at 37° C. for 45 minutes to assay β-galactosidase activity at 420 nm by colorimetry. The combined ratio of labelled glucagon to labelled glucagon fragment in each dilution concentration of antisera by immune reaction was determined.

(a) Labelled glucagon(1-29):

β-galactosidase labelled glucagon(1-29 ]40 μg as glucagon(1-29)] obtained by the method as hereinafter described was used.

(b) Labelled glucagon fragments:

β-galactosidase labelled glucagon(16-29), β-galactosidase labelled glucagon(17-29) and β-galactosidase labelled glucagon(19-29) prepared by the method hereinbelow were used in an amount of about 20 μg of each glucagon fragment.

(2) Results and discussion of immune reactivity:

The ratios of combination in immune reactivity calculated by the amounts of precipitate for each of the antisera are shown in the following table in the case of 800, 6400 and 51200 times dilutions. The combination ratios in the case of the remaining dilutions resemble these results.

In the Table:

+++: combination ratio: >75%,
++: combination ratio: 50-75%,
+: combination ratio: 25-50%,
−: combination ratio 0-25%.

As shown in the Table, glucagon(16-29) of the present invention resembles glucagon(17-29) and glucagon(19-29) in its structure; however the immune reactivity of antibodies in the antisera obtained by injection of each fragment show great differences.

Antibodies produced by glucagon(16-29) of the present invention showed sensitive and advantageous immune reactivity against not only glucagon(16-29) but also glucagon(17-29), glucagon(19-29) and glucagon(1-29).

These results show that C-terminal specific antibody (antibody titer) can be quantitatively determined by using the glucagon fragment of the present invention.

III. Preparation of labelled glucagon(1-29) and labelled glucagon fragments:

(1) Labelled glucagon(1-29):

Aqueous 100 mM EDTA (10 μl) and 0.1% 3-(2'-benzothiazolyl-dithio) propionate succinimide ester in dimethylformamide (264.4 μl) were added in glucagon(1-29) (1 mg) dissolved in 50 mM phosphate buffer (pH 8.0) (0.4 ml) and the mixture was reacted at 5° C. for one hour. The reaction mixture was passed through a Sephadex G-15 column (1.5×40 cm) for gel filtration and the passed fractions were collected to obtain a solution containing a derivative wherein was introduced a 3-(2'-benzothiazolyl-dithio) propionyl group in the amino group of glucagon(1-29).

β-galactosidase (product of Boehringer Mannheim GmbH) (2.78 mg) was added to a 50 mM phosphate buffer (pH 8.0) (2 ml) containing the derivative (25 μg) of 3-(2'-benzothiazolyl-dithio) propionyl glucagon(1-29), and the mixture was reacted at room temperature for one hour. The reaction mixture was passed through a column (1.5×90 cm) of Sephadex G-150 for gel filtration and the passed fractions were collected to obtain β-galactosidase labelled glucagon(1-29) wherein were combined the amino group of glucagon(1-29) and the thiol group in β-galactosidase.

(2) Labelled glucagon fragments:

Aqueous 100 mM EDTA (10 μl) and 0.1% 3-(2'-benzothiazolyl-dithio) propionate succinimide ester in dimethylformamide (625 μl) were added to glucagon(16-29) (0.5 mg) dissolved in 50 mM phosphate buffer (pH 8.0) (0.4 ml) and the mixture was reacted at 5° C. for one hour. The reaction mixture was passed through a Sephadex G-15 column (1.5×40 cm) for gel filtration and the passed fractions were collected to obtain a solution containing a derivative wherein was introduced a 3-(2'-benzothiazolyl-dithio) propionyl group in the terminal amino group of glucagon(16-29).

β-galactosidase (6.19 mg) was added to 50 mM phosphate buffer (pH 8.0) (2 ml) containing the derivative (25 μg) of 3-(2'-benzothiazolyl-dithio) propionyl glucagon(16-29), and the mixture was reacted at room temperature for one hour. The reaction mixture was passed through a column (1.5×90 cm) of Sephadex G-150 for gel filtration and the passed fractions were collected to obtain β-galactosidase labelled glucagon(16-29) wherein were combined the terminal amino group of glucagon(16-20) and the thiol group in β-galactosidase.

The above glucagon(16-29) was replaced by glucagon(17-29) and glucagon(19-29) and treated by the same procedure as above to produce β-galactosidase

TABLE

| glucagon and glucagon fragments for immunity | | antisera dilution | labelled compounds used for assay | | | |
|---|---|---|---|---|---|---|
| | | | β-galactosidase labelled glucagon (16-29) | β-galactosidase labelled glucagon (17-29) | β-galactosidase labelled glucagon (19-29) | β-galactosidase labelled glucagon (1-29) |
| the present invention | glucagon (16-29) | × 800 | ++ | ++ | +++ | +++ |
| | | × 6400 | ++ | ++ | +++ | ++ |
| | | × 51200 | + | + | + | + |
| Control | glucagon (17-29) | × 800 | − | − | + | + |
| | | × 6400 | − | + | + | + |
| | | × 51200 | − | − | − | − |
| | glucagon (19-29) | × 800 | − | − | − | − |
| | | × 6400 | − | − | − | − |
| | | × 51200 | − | − | − | − |
| | glucagon (1-29) | × 800 | + | + | ++ | ++ |
| | | × 6400 | + | + | + | ++ |
| | | × 51200 | − | − | − | + | labelled glucagon(17–29) and β-galactosidase labelled glucagon(19–29).

What is claimed is:

1. A process for the preparation of specific antibodies which comprises sensitizing a mammal by administering to said mammal a peptide of the formula H—Ser—Arg—Arg—Ala—Gln—Asp—
Phe—Val—Gln—Trp—Leu—Met—Asn—
Thr—OH conjugated with albumin or a modified albumin, collecting blood from the mammal, and concentrating said antibodies from said collected blood.

2. A process as claimed in claim 1, in which the peptide is conjugated with the use of glutaraldehyde or 3-(2′-benzothiazolyl-dithio) propionate succinimide ester as a conjugation reagent.

* * * * *